United States Patent [19]
Simon et al.

[11] Patent Number: 5,090,424
[45] Date of Patent: Feb. 25, 1992

[54] CONFORMABLE URETHRAL PLUG

[75] Inventors: John G. Simon, Boston; James E. Nicholson, Lincoln, both of Mass.

[73] Assignee: UroMed Corporation, Boston, Mass.

[21] Appl. No.: 636,285

[22] Filed: Dec. 31, 1990

[51] Int. Cl.⁵ .......................... A61F 5/48; A61F 2/00
[52] U.S. Cl. ......................... 128/885; 128/DIG. 25; 600/29
[58] Field of Search .................... 600/29–31; 128/885, 834, DIG. 25; 623/14

[56] References Cited

U.S. PATENT DOCUMENTS

| | | | |
|---|---|---|---|
| 2,494,393 | 1/1950 | Lamson | 600/29 |
| 2,638,093 | 5/1953 | Kulick | 128/DIG. 25 |
| 3,646,929 | 3/1972 | Bonnar | 600/29 |
| 3,841,304 | 10/1974 | Jones | 600/29 |
| 4,428,365 | 1/1984 | Hakky | 128/DIG. 25 |
| 4,846,784 | 7/1989 | Haber | 600/29 |

FOREIGN PATENT DOCUMENTS 8900030  1/1989  World Int. Prop. O. ........... 600/29

Primary Examiner—Robert A. Hafer
Assistant Examiner—Michael Brown
Attorney, Agent, or Firm—Lorusso & Loud

[57] ABSTRACT

The present invention is a device and method of using a device by patients who suffer from urinary incontinence. This device is a flexible urethral plug which has two components: a molded soft inflatable plastic catheter and a transportable fluid. The fluid can be moved from an external bellows, through a check valve to inflate and distend the device within the urethra, the bladder neck or the bladder causing the device to block the flow of urine through the urethra and assist the natural function of the sphincter in closing the urethra.

8 Claims, 4 Drawing Sheets

CONFORMABLE URETHRAL PLUG

BACKGROUND OF INVENTION

1. Field of Invention

The present invention is a novel urethral plug which can be inserted into the urethra to restrict the flow of urine through the urethra and is used by a person suffering from urinary incontinence. This device can be used by male or female patients.

2. Prior Art

Urinary stress incontinence is defined as the involuntary loss of urine when the pressure within the urethra exceeds the maximum urethral pressure in the absence of detrusor activity.

While the problem of stress incontinence occurs in both men and women, it predominantly occurs in women of childbearing age and beyond. The frequency of incontinence in women is approximately four times that of men. Less than one-third of women with moderate to severe incontinence are treated for the problem. While 25 to 41% of all women suffer some form of incontinence, 6 to 8% are troubled by the problem to the extent that they must wear diapers or sanitary napkins constantly.

There are in existence many methods and devices used to address the problem in involuntary loss of urine in people suffering from incontinence. Surgery is perhaps the most desirable method in cases of severe incontinence in younger patients. The surgical alternative often involves a procedure whereby the neck of the bladder is reduced by suspending the bladder. However, there are numerous well known risks associated with this as well as any surgical procedure. For some patients, surgery is not recommended for medical or other reasons, and for those with mild incontinence surgery is not an appropriate solution. The expense of surgery is also a factor to be considered.

Incontinence can also be treated with various medications as well as exercises. These methods vary depending whether the patient is male or female. The most commonly used device for both sexes is the diaper which simply catches and absorbs the urine involuntarily voided. This device obviously does not alleviate the problem of incontinence and has many hygienic and aesthetic drawbacks. Leakage occurs frequently, and there is no control over the voiding of urine. For women, rigid devices, such as tampons, were suggested. Such rigid devices must be inserted into the vagina to support the urethra. These types of rigid devices are difficult to fit and thus require medical assistance in fitting. There are also in existence prosthetic urethral valves, which require surgical implantation and invite numerous complications. Foley drainage catheters and drainage bags are also known, but these devices have many disadvantages.

The following discussion addresses the problems with devices taught by prior art.

U.S. Pat. No. 4,457,299 to Corewell teaches an internally prestressed capsule device which is inserted into the urethra. This device can be used by both men and women. The prestressed capsule deforms the lower interior of the urethra into a broadly elliptical shape, and the capsule is set at a prestressed pressure slightly above the involuntary pressure. When the urine pressure exceeds the preset pressure of the capsule, the capsule deforms allowing the urine to flow around the device. When voiding ceases, the device returns to its prestressed position and configuration. As an indwelling device, the device faces the problems of encrustation and infection. Also, no mechanism for anchoring the device in place is described, and it is not clear that one could anchor a device such as this in place, seal off the urine and leave the urethra unharmed. In addition, there is a need to measure the diameter of the patient's urethra and perform pressure testing before this device can be used.

U.S. Pat. No. 4,553,533 to Leighton teaches a prosthetic urethral sphincter valve which is placed in the urethra and anchored in the bladder. The valve is composed of a spring, an annular guide, a diaphragm and a grease filled bag member. The patient increases his bladder pressure by means of a valsalva maneuver, and holds this pressure while the valve activates. The urine passes through the valve, and then the spring returns to its collapsed position when the bladder pressure is released. This device is relatively expensive and complicated, requiring that it be used for a relatively long time in order to make it economically feasible. It appears that this device would be uncomfortable for the patient. Furthermore, no means for anchoring the device to prevent its migration into the bladder is provided. As an indwelling device, it is subject to infection, encrustation and irritation. Due to the complexity and location of the device, it must be inserted under the guidance of a physician.

In somewhat unrelated art but art of interest, U.S. Pat. No. 4,682,592 to Thoregard describes a device which achieves reversible male sterilization. This device is a hollow elongated tube with an expandable elastic cap forming a fluid tight seal at one end and a plug which forms a seal on the other end. In one embodiment, the device is inserted though the urethra to temporarily block the passage of sperm. In the second embodiment, a smaller plug is inserted into the juncture of ejaculatory ducts with the urethra or into the vas deferens. The second embodiment requires implantation by a physician. The device described by Thoregard never gets near the bladder neck or the bladder.

International Patent Application No. PCT/GB88/00464 to Prosthex, Ltd., teaches an incontinence device for use by women. This device is a sponge tampon which is inserted into the vagina. This device is supposed to exert pressure on the urethra, but it does not prevent involuntary voiding. It does not stop or plug the urethral opening.

Nielsen, Kurt K. et al, "The Urethral Plug: A New Treatment Modality for Genuine Urinary Stress Incontinence in Women", *J. Urology*, Vol. 44, p. 1199 (1990). This paper describes a device to be used by women which consists of one or two solid spheres of 7 mm in diameter, located along a 3 mm soft shaft. A thin and soft plate is used to anchor the device at the meatus urinarius or the opening of the urethra. The meatal plate is located normal to the end of the device to prevent the plug from being drawn into the urethra. One sphere is located upstream of the maximum urethral closing pressure point, corresponding to the location of the sphincter. In the two sphere embodiment, the second sphere is located with its midpoint at the bladder neck, and is used to assist in reducing urinary flow and pressure transmission to the urethra that the sphincter can operate. When the patient wants to void, the plug is removed and then a new one inserted.

One problem with this device is that the patient must have three urethral closure pressure profiles performed before the device is inserted in addition to various other examinations. This is done in order to locate the urinary sphincter. The device is then custom made for each patient based on the profiles and according to their anatomy. This device is made from Kraton G, a non-toxic thermoplastic elastomer. Additional problems were associated with the use of this device. Patients often lost the plug showing inadequate anchoring. Some could not learn how to insert it and there were difficulties with the placement of the distal sphere. In addition, there is no sealing mechanism to prevent urine outflow, so that the device must depend on the body's own sealing mechanism. This presents a problem, because there is a significant population without such capabilities.

The devices and methods described above present many unsolved problems and various drawbacks. Thus, a great need exists for a device and method for treating urinary incontinence in both men and women.

SUMMARY OF THE INVENTION

The present invention involves a device for use by women and men suffering from urinary incontinence.

The device, in accordance with the present invention, is a flexible urethral plug which has two components: a molded soft inflatable plastic catheter and a transportable fluid. The fluid can be moved from an external bellows, through a check valve to inflate and distend the device within the urethra, bladder neck o bladder causing the device to block the flow of urine through the urethra and assist the natural function of the sphincter in closing the urethra.

Accordingly, it is an object of the present invention to provide a urethral plug which prevents involuntary voiding of urine.

It is another object of the present invention to provide a method of using a urethral plug by patients suffering from urinary incontinence.

It is yet another object of the present invention to provide a method of using a urethral plug which allows one to prescribe and then insert a plug without first determining the location of the urinary sphincter.

It is still another object of the present invention to provide a method of using a removable-to-void urethral plug which is expanded in order to keep it in place when it is in the body.

Other objects and advantages of the invention will become apparent from the descriptions of the drawings and the preferred embodiments, which follow.

DETAILED DESCRIPTION OF THE PREFERRED EMBODIMENTS

Figure 1:
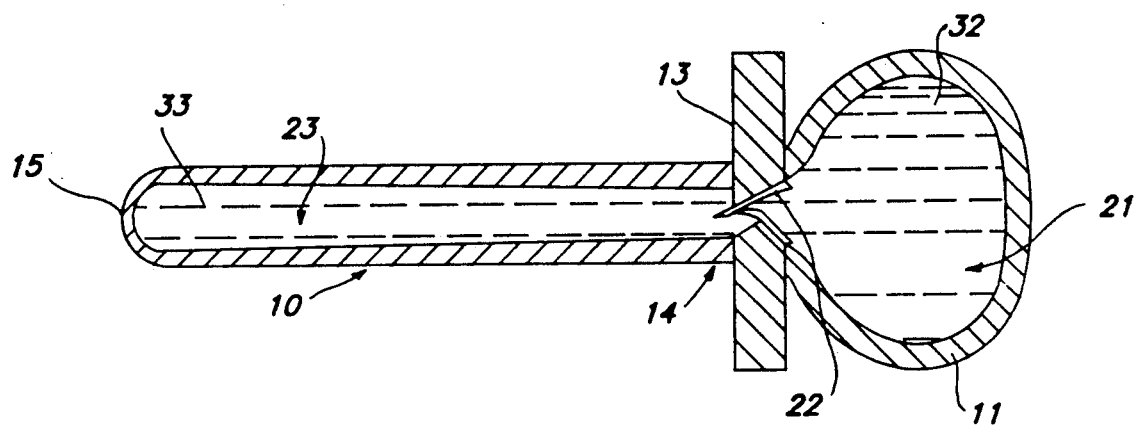
FIG. 1 is a cross-sectional view showing the urethral plug in a deflated insertable configuration.

At the outset, the invention is described in its broadest overall aspects with a more detailed description following.

The present invention is a device for treatment of incontinence in men and women and a method for using the device to stop unwanted flow of urine. While this invention will be used for any type of urinary incontinence, it will be particularly useful for stress incontinence.

The urethral plug, which is the subject of this invention, is a soft, flexible device which is inserted into the patient's urethra. It conforms to the shape and size of the urethra, especially upstream of the sphincter, toward the bladder neck. There is no need to custom make the device for each individual, although the device may be manufactured in several lengths and sizes. The patient's urethral length is measured by a physician to ensure that the proper size plug is used.

Preferably, the plug is made from a material such as Kraton G (Trademark for a styrene-butadiene elastomer), but of course other biocompatible soft elastomers can be used. The choice of material forms no part of the invention. The plug has a hollow inner core with an increasing internal diameter toward the bladder neck. At the proximal end of the device there is an expandable sack, and at the distal end there is an inflatable balloon with a check valve. The check valve is located within a meatal plate, and said plate will anchor the plug at the meatus urinarius. The device is inserted into the urethra, so that the inflatable balloon is left outside the body, and the sack into inserted into the urethra, remains in bladder neck or bladder.

The hollow inner core is filled with a fluid, however, it can be air. When the device is inserted, the patient squeezes the inflatable balloon filled with the fluid, thus moving the fluid through the check valve into the sack at the proximal end. The inflated sack forms a plug by blocking the passage in the urethra, the bladder neck or the bladder itself. When the patient wishes to void, a gentle tug on the external part of the device will cause misalignment of the valve, and the fluid will move back down out of the sack into the balloon. Then, the device can be removed. After voiding, the patient reinserts the device, squeezes its balloon again and causes blockage of the urethra, the bladder neck or the bladder until the next time he or she wishes to void.

In one embodiment the device is disposable, and the plug is made from Kraton G which tends to remember its shape and is not easily reused.

In another embodiment, the plug is made from a silicone material which can be easily washed after each use and thus reused. In both embodiments, the preferred fluid is a silicone gel although air can be employed as the fluid.

Additionally, the device may be a combination of disposable and reusable parts and can be inflated by an external pump.

Additionally, the device can be deflated by communication of the proximal cavity with a second valve specifically for relief.

Although FIGS. 1-10 are shown with respect to the female anatomy, this device can be used for men. In addition, the drawings are not done to scale.

One embodiment of the device of the present invention is shown in FIG. 1 where a urethral plug 10 is shown. A bellows 11 defines cavity 21, and is used to transport fluid 32 contained in cavity 21 through a check valve 22 which is located within meatal plate 13. The bellows is made from a material which makes it conformable to the body and comfortable for the patient when the urethral plug is in place. The fluid 32 is transported to cavity 23 located within plug 10 becoming fluid 33. The wall of the plug is relatively constant in outer diameter allowing the device to be easily inserted. However, the wall thickness varies from the meatal plate 13, beginning at location 14 to the proximal end 15 where the wall is thinnest, allowing the greatest inflation. The fluid 32 can be any fluid which can be pumped from cavity 21 to cavity 23 through check valve 22.

Figure 2:
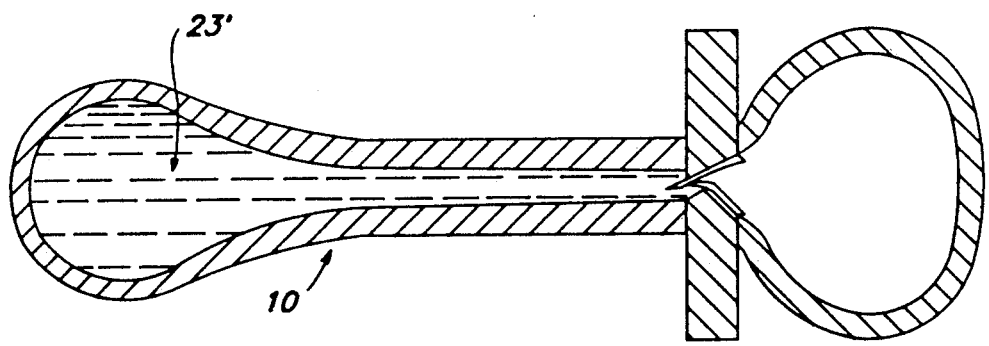
FIG. 2 is a cross-sectional view showing the urethral plug in an inflated configuration.
Figure 3:
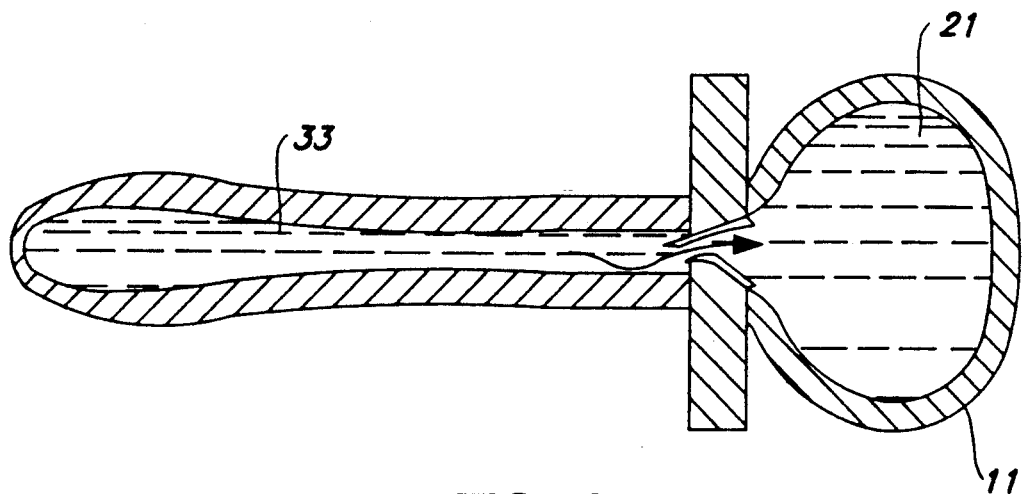
FIG. 3 is a diagrammatic representation of a method for deflating the urethral plug.
Figure 4:
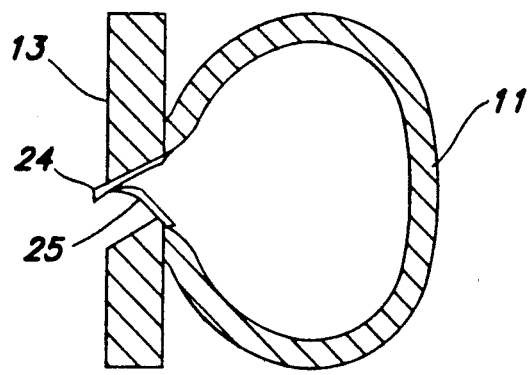
FIG. 4 is a cross-sectional view of the check valve used in the plug of the present invention in a closed position.
Figure 5:
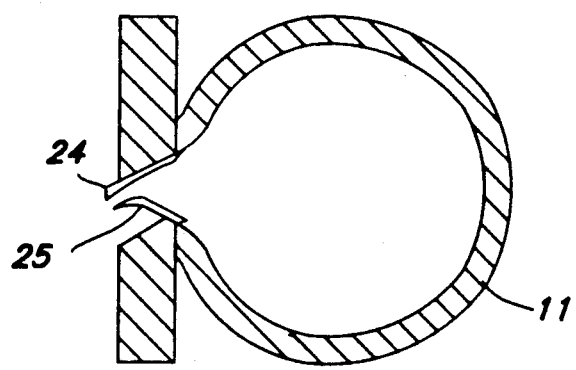
FIG. 5 is a view similar to that shown in FIG. 4 but showing the check valve in an opened position.

Check valve 22, shown in FIGS. 4 and 5, is designed to be asymmetric, functioning as a normal check valve. When bellows 11 is squeezed, fluid 32 is pumped from cavity 21 through valve 22. FIG. 2 shows cavity 23 inflated to a new configuration 23'. When it is desired to deflate cavity 23', the patient simply tugs on bellows 11 causing valve 22 to intentionally misalign, allowing fluid 33 to substantially return to cavity 21 such that there is pressure equilibrium between cavity 21 and cavity 23.

FIG. 4 shows the intentional misalignment which is caused by leaf 24 being connected to metal plate 13 such that it deflects minimally. On the other hand, leaf 25 is relatively flexible such that it moves in response to a patient-initiated tug on bellows 11, causing leaf 25 to separate from leaf 24. FIG. 5 shows leaf 25 separated from leaf 24. Thus, fluid may pass reversibly from cavity 23 back to cavity 21 through check valve 22 when bellows 11 is tugged upon.

A distinct advantage of the present invention is the fact that this device is conformable to the shape of the urethra. This device does not require urethral peak pressure profiles or other tests to determine the shape of the urethra. The device responds to the urethral shape with preferential distal expansion to assist its locking in the urethra, bladder neck or bladder. The plug can be easily inserted and removed by the patient, and it is intended to be inexpensive. Another distinct advantage of this device is that a seal is obtained without stretching the anatomy of the patient upon insertion. Furthermore, the use of a simple inflatable/deflatable device allows one to seal off the urine flowing from the bladder and also to anchor the device securely. The anchoring feature is extremely important in assuring proper functioning of this type of device. The sealing feature is particularly important in patients whose own natural sealing function is impaired.

The urethral plug, according to the present invention, is made of soft material so that discomfort and irritation are minimized. The device is made from commonly used medical grade materials which have a long history of biocompatibility. Infection is not expected to be a problem when the device is to be frequently exchanged for a clean one or if disposable, a new one. It has hygienic and aesthetic advantages in that no leakage occurs, and the patient is not forced into wearing diapers, sanitary napkins or the like.

The following example further illustrates the invention.

EXAMPLE 1

Figure 6:
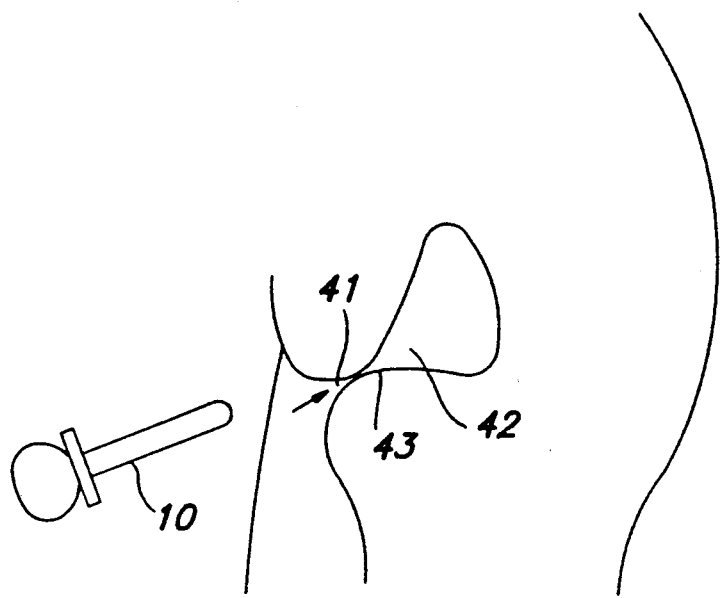
FIG. 6 is a diagram showing the method of inserting the urethral plug into the urethra.
Figure 7:
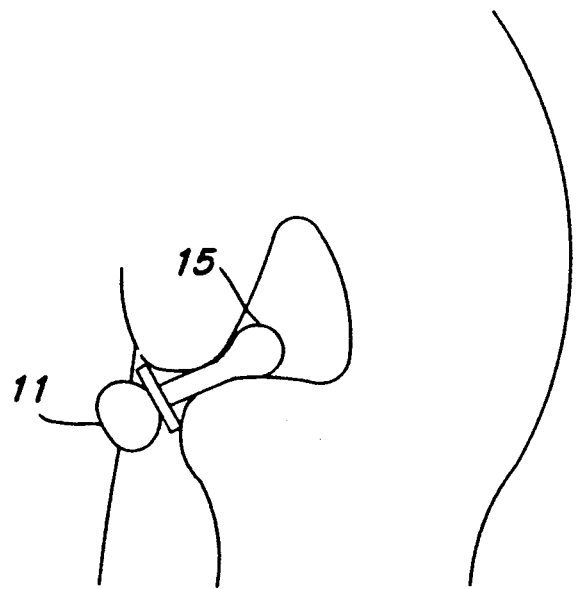
FIG. 7 is a diagram showing the urethral plug positioned within the urethra.

As shown in FIG. 6, the deflated urethral plug 10 is inserted into the patient's urethra 41. After insertion, as shown in FIG. 7, bellows 11 is pumped by the patient so that the distal end preferentially expands into space 42 beyond sphincter 43 and/or into the bladder neck or bladder thus causing the device to assist in sealing the urethra. For removal, bellows 11 is gently tugged on by the patient so that the expanded proximal end 15 deflates, thereby allowing urethral plug 10 to be easily removed from the urethra 41.

The device is sized to 14 Fr. or 0.184 inch diameter (4.7 mm) which is typically the size of a woman's urethra, although it may be sized otherwise. The wall thickness of the plug varies from the meatal plate to the tip of the device. At the meatal plate, the wall thickness is nominally 0.070 inches but may vary from 0.050 inches to 0.075 inches depending upon the elasticity desired. At the innermost position, the wall thickness may be in a range of 0.002 inches to 0.020 inches depending upon the degree of wall expansion desired within the urethra, bladder neck or bladder. Variation of the wall thickness changes the shape of the proximal end of the device when inflated.

The meatal plate is 1 cm in diameter and 1 mm thick. The plate is composed of two 0.5 mm halves formed by molding the plug and valve mechanisms separately. The outer material making u the plug is Kraton G. Materials well known in the art are used to manufacture all other parts of the device.

Figure 8:
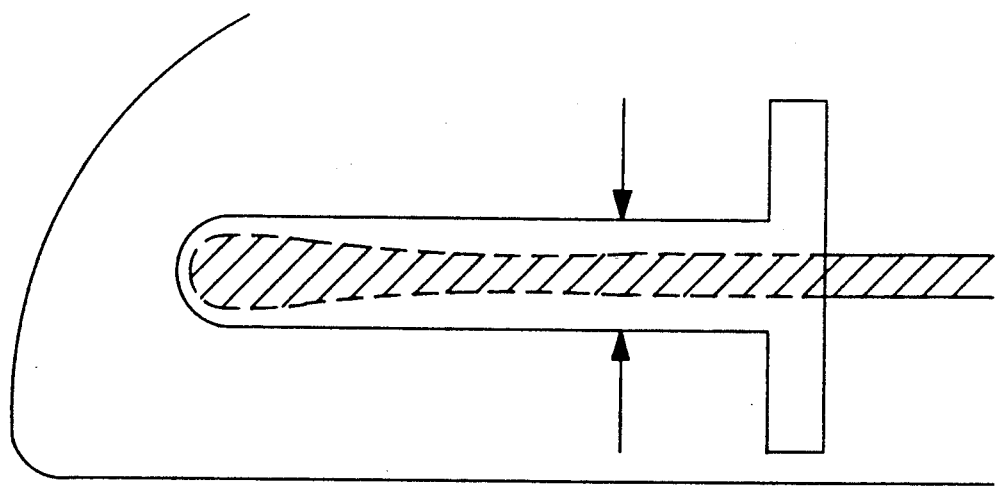
FIG. 8 is a diagram showing a mold used to manufacture the urethral plug of the present invention.

The outer plug element is molded in three parts. As shown in FIG. 8, the first part is the plug which can be molded around a central core which creates a variable wall thickness by its position within the mold cavity. The molding material, Kraton G, is normally injection molded. Silicone is static molded and then heated in an oven to cause curing of the rubber.

Figure 9:
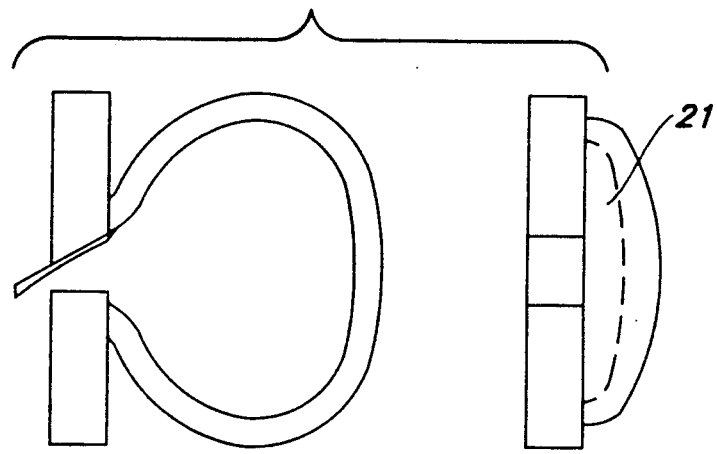
FIG. 9 is a diagram showing the method for molding the right half of the check valve.
Figure 10:
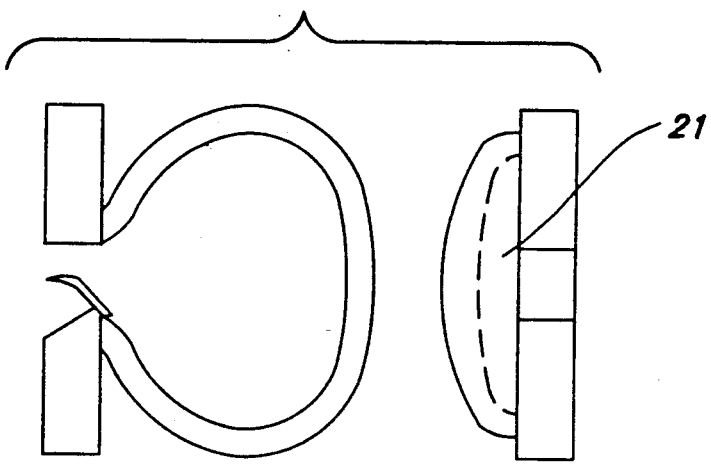
FIG. 10 is a diagram showing the method for molding the left half of the check valve.

The second and third elements to be molded are right and left halves of the asymmetric valve, shown in FIGS. 9 and 10. The right half, as shown in FIG. 9, is designed with a relatively stationary valve element. The left half, as shown in FIG. 10, is designed with a valve element which moves in response to tugging on the distal end of the valve. The two halves are matched so that when assembled they form a check valve. During use, bellows 11 is pumped by the patient, forcing fluid through the valve element.

The three components can be assembled by the use of adhesives or any such well known means. Then, the fluid can be injected into the cavity 21 for later use by the patient. Alternatively, the fluid can be injected by the patient when desired. In this embodiment, air would be pumped into the plug until sealing of the urethra, bladder neck or bladder is achieved. This embodiment of the device does not represent a closed system, as the device is pressurized by the patient and not during the manufacturing process.

The invention may be embodied in other specified forms without departing from the spirit of essential characteristics thereof. The present embodiments are therefore to be considered in all respects as illustrative and not restrictive. The scope of the invention is indicated by the appended claims rather than by the foregoing description, and all changes which come within the meaning and range or equivalency of the claims are theretofore intended to be embraced therein.

What is claimed is:

1. A removable device for blocking unwanted flow of urine comprising:
   (a) an expandable housing forming a plug portion of the device which conforms to the shape of the urethra and defines an inner core which can accept a fluid;
   (b) means for the wearer to insert the device to achieve continence including means for introducing fluid into the inner core to cause the configuration of the outer housing to distend sufficiently to reduce the flow of urine from a bladder when the device is inserted into a urethra by the wearer; and
   (c) means for the wearer to remove the device to void including means for removing fluid in the core of the plug portion of the device so that the plug can be removed from the urethra by the wearer.

2. The device as set forth in claim 1 wherein the means for introducing fluid into the inner core includes a check valve in fluid communication with the inner core which permits flow of fluid through the check valve into the inner core.

3. The device as set forth in claim 2 wherein the means for introducing fluid into the inner core includes a bellows filled with fluid in fluid communication through the check valve with the inner core.

4. A method for preventing an unwanted discharge of urine comprising the following steps:
   (a) providing an expandable plug which can be inserted into the urethra;
   (b) inserting the expandable plug into the urethra;
   (c) expanding the plug in the urethra to restrict the flow of urine from the bladder through the urethra; and
   (d) deflating and removing the plug from the urethra when discharge of urine is desired.

5. A method for preventing an unwanted discharge of urine without first determining the location of the urinary sphincter comprising:
   (a) selecting an expandable plug which has been determined to conform to the length of the urethra;
   (b) inserting the expandable plug into the urethra;
   (c) expanding the plug in the urethra to restrict the flow of urine from the bladder through the urethra; and
   (d) deflating and removing the plug from the urethra when discharge of urine is desired.

6. A removable device for blocking unwanted flow of urine comprising:
   (a) an expandable housing forming a plug portion of the device which conforms to the shape of the urethra and defines an inner core which can accept a fluid;
   (b) means for the wearer to insert the device to achieve continence including means for introducing fluid into the inner core to cause the configuration of the outer housing to distend sufficiently to reduce the flow of urine from a bladder when the device is inserted into a urethra by the wearer wherein the means for introducing fluid into the inner core includes a check valve in fluid communication with the inner core which permits flow of fluid through the check valve into the inner core, and a bellows filled with fluid in fluid communication through the check valve with the inner core; and
   (c) means for the wearer to remove the device to void including means for removing fluid in the core of the plug portion of the device so that the plug can be removed from the urethra by the wearer;
   (d) a meatal plate which is used to anchor the device at the meatus urinarius, and is attached to the bellows with the check valve positioned within the meatal plate.

7. The device as set forth in claim 6 wherein the means for removing fluid in the inner core includes two leaves which comprise the check valve which separate when the check valve is misaligned so the fluid returns through the check valve into the bellows.

8. The device as set forth in claim 6 wherein the means for removing fluid in the inner core further includes a distended portion which tends to return to its original undistended shape.

* * * * *